United States Patent [19]

Dumbroff et al.

[11] Patent Number: 5,087,417
[45] Date of Patent: Feb. 11, 1992

[54] CONTROL OF SENESCENCE IN FRUITS, VEGETABLES AND FLOWERS

[75] Inventors: Erwin B. Dumbroff, Waterloo; John E. Thompson, Guelph, both of Canada; Ching Y. Shih, Davis, Calif.

[73] Assignee: University of Waterloo, Canada

[21] Appl. No.: 322,479

[22] PCT Filed: Oct. 8, 1987

[86] PCT No.: PCT/US87/02557
§ 371 Date: Aug. 4, 1988
§ 102(e) Date: Aug. 4, 1988

[87] PCT Pub. No.: WO88/02602
PCT Pub. Date: Apr. 21, 1988

[30] Foreign Application Priority Data
Oct. 8, 1986 [GB] United Kingdom ................ 8624100

[51] Int. Cl.$^5$ ................................................ A01N 3/02
[52] U.S. Cl. .................................. 422/1; 47/58; 71/68; 71/84; 422/40
[58] Field of Search ............ 422/1, 40; 71/68, 79, 71/84; 47/58

[56] References Cited
U.S. PATENT DOCUMENTS
3,169,849 2/1965 Lemin ........................ 71/84

4,388,473 6/1983 Richter et al. .................. 560/21 X

Primary Examiner—Jill Johnson
Attorney, Agent, or Firm—Shoemaker and Mattare, Ltd.

[57] ABSTRACT

Senescence in perishable plant tissue is inhibited by the application thereto of an effective amount of a compound of the formula:

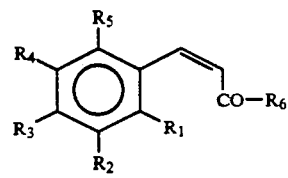

wherein $R_1$, $R_2$, $R_3$, $R_4$ and $R_5$ are each selected from the group consisting of hydrogen, —OH or —OR$_7$, provided that at least one of $R_1$ to $R_5$ is a hydroxyl group, $R_6$ is selected from the group consisting of —OH, —OR$_8$ and —NHR$_9$, $R_7$ is a substituent group, $R_8$ is the residue of an ester-forming compound and $R_9$ is the residue of an amide-forming compound. The compound may be prepared synthetically and, in some cases, can be isolated from natural sources, for example, the glucose ester of ferulic acid may be isolated from carnation petals.

7 Claims, 1 Drawing Sheet

CONTROL OF SENESCENCE IN FRUITS, VEGETABLES AND FLOWERS

FIELD OF INVENTION

The present invention relates to the inhibition of ethylene formation from perishable fruits, vegetables and flowers, thereby inhibiting the onset of senescence therein.

BACKGROUND TO THE INVENTION

Once fruits, vegetables and flowers are harvested, they are vulnerable to spoilage and must be consumed within a certain period of time. Some fruits and vegetables, for example, apples, can be stored under cold conditions for long periods without spoilage. Most fruits and vegetables, however, are perishable and cannot be stored for protracted periods.

Studies have been made of the mechanism of senescence and post-harvest deterioration. Membrane deterioration mediated by lipoxygenase has been identified as an early manifestation of the onset of senescence. Senescence is accompanied by the evolution of ethylene and once ethylene evolution commences, the process of deterioration is accelerated.

The biosynthetic path to ethylene formation has been identified as initial conversion of methionine to S-adenosyl methionine (SAM), the conversion of SAM to 1-amino-cyclopropane-1-carboxylic acid (ACC), and thence to ethylene.

It has previously been observed that the cytosol fraction from extraction of the petals of senescing carnation flowers inhibited ACC to ethylene conversion activity of membranes isolated from the petals (Mayak et al, Planta (1981) 153:49–55).

We have now been able to isolate and identify the active material which provides the inhibition and have identified a class of compounds which are useful in the inhibition of ethylene production in vitro and in situ from harvested fruits, vegetables and flowers.

SUMMARY OF INVENTION

In accordance with the present invention, there is provided a method of inhibiting senescence in perishable plant tissue, including fruits, vegetables and flowers, by the application thereto of an effective amount of a compound of the formula:

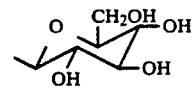

(I)

wherein $R_1$, $R_2$, $R_3$, $R_4$ and $R_5$ are each hydrogen, —OH or —$OR_7$ provided that at least one of $R_1$ to $R_5$ is a hydroxyl group, $R_6$ is —OH, —$OR_8$ or —$NHR_9$, $R_7$ is a substituent group, usually an alkyl group, or a sugar via an ether linkage, $R_8$ is the residue of an ester-forming compound, and $R_9$ is the residue of an amide-forming compound.

BRIEF DESCRIPTION OF DRAWING

The sole FIGURE of the drawing is a schematic flow sheet of the procedure used to effect isolation of the active component and as set forth in detail in Example 1 below.

GENERAL DESCRIPTION OF INVENTION

Figure 1:
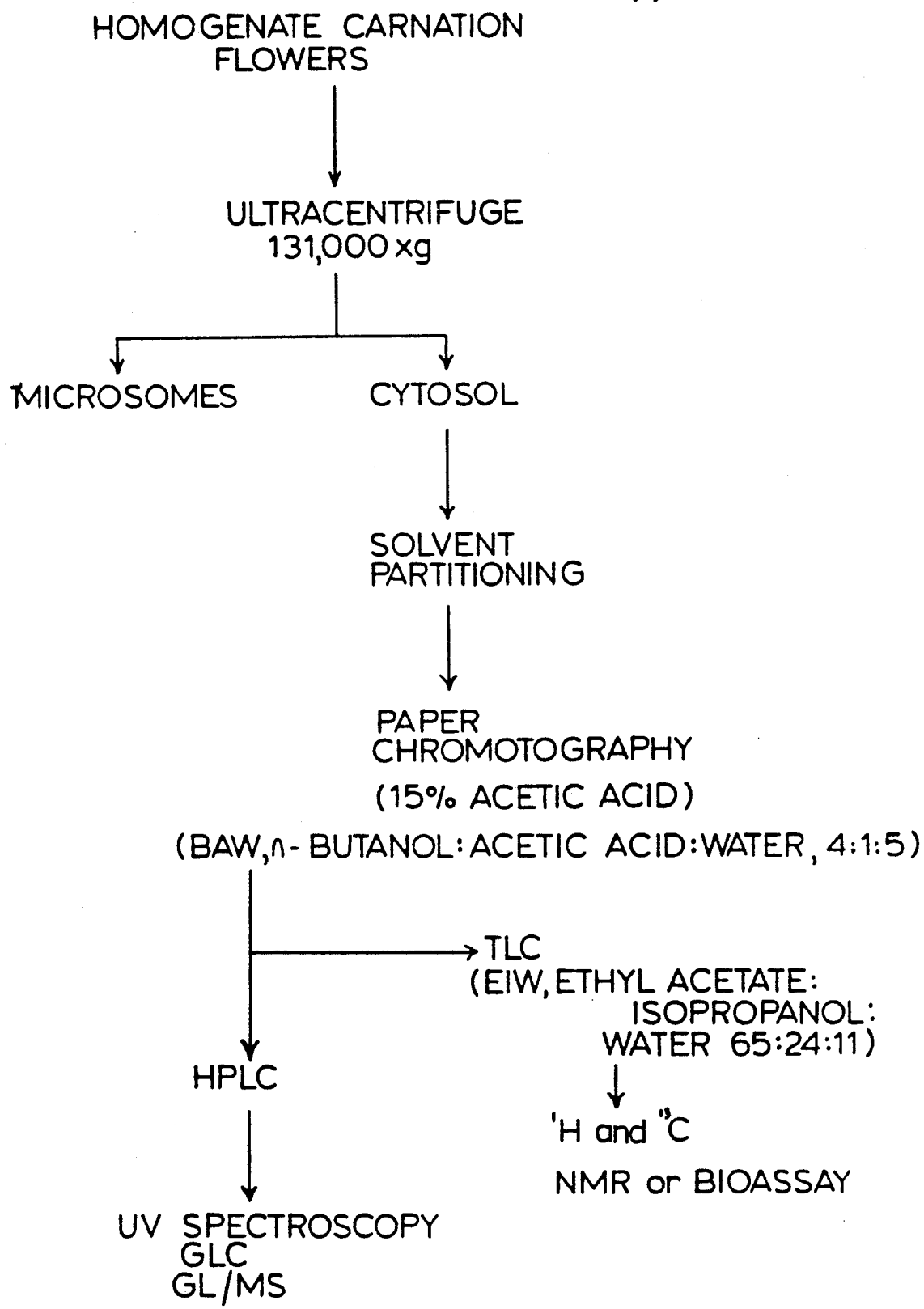

As noted above, the present invention resides in the application to perishable plant tissue of an effective amount of a compound of formula (I). In the compounds of formula (I), $R_7$ usually is a methyl or an ethyl group. Usually one only of the $R_1$ to $R_5$ groups is hydroxyl, while another of the $R_1$ to $R_5$ groups is alkoxy. Preferably, the organic acid, esterified or otherwise, is ferulic acid, i.e. the compound of formula (I) wherein $R_1$, $R_2$ and $R_5$ are hydrogen, $R_3$ is —OH and $R_4$ is —$OCH_3$. The organic acid also may be a benzoic acid derived by side-chain degradation of respective hydroxycinnamic acid precursors.

In the compounds of formula (I), the free acid may be used, i.e. $R_8$ is hydrogen, but it has been found that esters of the acids are preferred, especially esters having a plurality of hydroxyl groups. In one embodiment, $R_8$ may be a glycosyl ester, such as a glucose ester, for example, the compound wherein $R_8$ is B-D-glucose, i.e.:

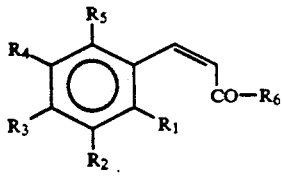

Multiples and mixtures of sugars may comprise the glycosyl group. Another example of an $R_8$ group is the ester of quinic acid.

The compounds used in the present invention may be isolated from natural sources. For example, the glucose ester of ferulic acid may be isolated from carnation petals by conventional isolation procedures involving chromatography. Such compound has been identified as the active compound achieving the inhibition reported in the previous work.

Some of the compounds, for example, ferulic acid, are available commercially, while others and their esters may be synthesized from commercially-available materials.

The compounds may be applied to the plant material with respect to which inhibition of ethylene production is desired in any convenient manner, usually from aqueous solutions thereof, for example, by infusion. Generally, only small amounts are required to achieve long term inhibition of lipoxygenase and ethylene production.

The active compounds disclosed herein have been shown to inhibit ethylene formation and lipoxygenase activity in carnation petals. Since the same mechanism of senescence applies in fruits and vegetables, the compounds should have the same inhibitory effect on such other materials.

Feruloyl glucose has shown promise as a full radial scavenger in tests with a chemical system and, therefore, this compound and other similar phenols may prove useful as processed food preservatives.

EXAMPLES

In the Examples, reference is made to the accompanying drawing (FIG. 1), which is a schematic flow sheet of the process steps used to effect isolation of the active component.

Example 1

This Example illustrates the isolation of the glucose ester of ferulic acid from senescing carnation flowers.

50 g of senescing carnation petals were homogenized and centrifuged at ultraspeed (131,000×g). The supernatant (100 ml), was freeze dried to a yellowish powder (2.5 g). The lyophilyzed samples (250 mg) were extracted with 80% methanol at 4° C. Solid material was removed by centrifugation at top speed in a clinical centrifuge. After decanting, the pellet was resuspended in cold 80% methanol and centrifuged again. The washing procedure was repeated until the pellet was white and the supernatant was clear.

The combined methanolic fractions were evaporated under vacuum to an aqueous volume (10 ml), adjusted to pH 2.0 with 0.4 M HCl and immediately extracted four times with ethyl acetate. The combined ethyl acetate fractions were dried and the residue redissolved in 300 µl of absolute methanol and referred to as the crude ethyl acetate extract.

The crude ethyl acetate extract was strip-loaded on 15×57 cm sheets of Whatman No. 3 filter paper and developed by descending chromatography with 15% (v/v) acetic acid. The inhibitory strip ($R_f$=0.81) was eluted and rechromatographed using n-butanol:acetic acid:water (BAW, 4:1:5, v/v/v). The inhibitor, purified by two systems of paper chromatography, was purified further by preparative TLC using ethyl acetate:isopropanol:water, (65:24:11, v/v/v). The location and identity of the inhibitor was monitored by $R_f$ values and UV fluorescence of the appropriate region on the chromatogram. Further confirmation was obtained from a complete UV scan of the eluates from each TLC plate. These procedures are illustrated in FIG. 1. The inhibitor was identified as the glucose ester of ferulic acid.

Example 2

This Example illustrates the inhibition of ethylene formation in vitro by the glucose ester of ferulic acid.

Microsomes from senescing carnation flowers were treated with varying quantities of the glucose ester of ferulic acid, isolated as described in Example 1, and the production of ethylene was determined as a percentage of the control production of ethylene in the absence of added ferulic acid ester The results obtained are set forth in the following Table I:

TABLE I

| Reaction Mixture | Ethylene Production (nl.100 µg$^{-1}$ protein h$^{-1}$) | % Control |
|---|---|---|
| Control | 0.962 ± 0.03 | 100 |
| Control + 10 µM of Additive | 0.518 ± 0.019 | 53.9 |
| Control + 50 µM of Additive | 0.014 ± 0.005 | 2.0 |
| Control + 100 µM of Additive | 0 | 0 |

As may be seen from this Table I, a concentration of only 100 µM of the glucose ester of ferulic acid was sufficient to decrease ethylene formation to zero.

Example 3

This Example illustrates the use of the glucose ester of ferulic acid for in vivo prevention of ethylene formation in carnations.

The glucose ester of ferulic acid (1 mM), isolated as described in Example 1, was taken up transpirationally into petals of carnation flowers. Ethylene production was determined as a percentage of the ethylene produced by untreated control petals at various times after incubation with ACC.

The results obtained are set forth in the following Table II:

TABLE II

| Time after Treatment (hrs) | % Inhibition |
|---|---|
| 12 | 100 |
| 16 | 97.3 |
| 21 | 90.4 |
| 26 | 81.7 |

As may be seen from the data presented in Table II, the effectiveness of preventing ethylene formation is retained over a long period of time.

Example 4

This Example illustrates the inhibition of lipoxygenase (LOX) activity by the glucose ester of ferulic acid.

Lipoxygenase activity has been demonstrated in microsomal membranes of carnation (Lynch et al., Planta 1985, 164:121-125) and microsomes and cytosol fractions of bean cotyledon (Lynch and Thompson, FEBS 1984, 173:251-254). The addition of the glucose ester of ferulic acid, isolated as described in Example 1, to both membrane and cytosol preparations caused an inhibition of enzyme activity in all experiments when 100 µm concentrations were used.

The results obtained are set forth in the following Table III:

TABLE III

Effect of feruloyl glucose on the activity of lipoxygenase in carnation and bean. All the experiments were repeated at least twice. The data reported are means from one experiment, where n = 3.

| Experiment | Components in reaction mixture | Lipoxygenase activity (% of control) |
|---|---|---|
| 1.a. | control, containing 100 µg membrane protein from Stage IV carnation | 100 |
| b. | membrane plus 40 µM feruloyl glucose (FG) | 1.8 |
| 1.a. | control, containing 60 µg membrane protein of 9 d bean cotyledon | 100 |
| b. | membrane plus | |
| | 50 µM FG | 46.3 |
| | 100 µM FG | 37.8 |
| 3.a. | control, containing 10 µg cytosol protein of 9 d bean cotyledon | 100 |
| b. | cytosol plus | |
| | 50 µM FG | 48.4 |
| | 100 µM FG | 35.9 |

As may be seen in Table III. feruloyl glucose was most effective against lipoxygenase activity derived from carnation, with almost complete inhibition of activity with a 40 µM solution of the inhibitor, but FG was also effective against LOX from several other plant systems including bean cotyledons.

SUMMARY OF DISCLOSURE

In summary of this disclosure, the present invention provides a novel method of inhibiting the onset of senescence in harvested fruits, vegetables and flowers by the application of small quantities of certain phenolic derivatives. Modifications are possible within the scope of this invention.

What we claim is:

1. A method of inhibition of senescence in harvested perishable plant tissue, which comprises:

applying to said harvested perishable plant tissue an effective amount of a compound of the formula:

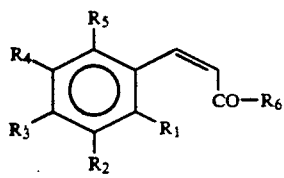
(I)

wherein $R_1$, $R_2$, $R_3$, $R_4$ and $R_5$ are each selected from the group consisting of hydrogen, —OH or —$OR_7$, provided that at least one of $R_1$ to $R_5$ is a hydroxyl group, $R_6$ is selected from the group consisting of —OH, —$OR_8$ and $NHR_9$, $R_7$ is a substituent group, $R_8$ is the residue of an ester-forming compound and $R_9$ is the residue of an amide-forming compound.

2. The method of claim 1 wherein at least one of $R_1$ to $R_5$ is $OR_7$ and $R_7$ is selected from the methyl group and the ethyl group.

3. A method of inhibition of senescence is perishable plant tissue, which comprises:

applying thereto an effective amount of a compound of the formula:

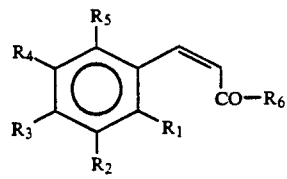
(I)

wherein $R_1$, $R_2$, $R_3$, $R_4$ and $R_5$ are each selected from the group consisting of hydrogen, —OH or —$OR_7$, provided that only one of the groups $R_1$ to $R_5$ is hydroxyl and another of the groups $R_1$ to $R_5$ is alkoxy, $R_6$ is selected from the group consisting of —OH, —$OR_8$ and —$NHR_9$, $R_7$ is selected from the methyl group and ethyl group, $R_8$ is the residue of an ester-forming compound and $R_9$ is the residue of an amide-forming compound.

4. A method of inhibition of senescence in perishable plant tissue, which comprises:

applying thereto an effective amount of a compound of the formula:

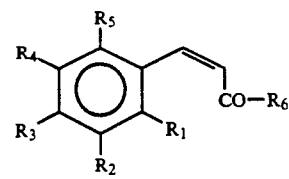
(I)

wherein $R_1$, $R_2$ and $R_5$ are each hydrogen, $R_3$ is —OH and $R_4$ is —$OCH_3$, $R_6$ is selected from the group consisting of —OH, —$OR_8$ and —$NHR_9$, $R_7$ is a substituent group. $R_8$ is the residue of an ester-forming compound and $R_9$ is the residue of an amide-forming compound.

5. The method of claim 4 wherein $R_6$ is —$OR_8$ and $R_8$ is a glycosyl ester.

6. The method of claim 5 wherein $R_8$ is B-D-glucose.

7. The method of claim 5 wherein $R_8$ is an ester of quinic acid.

* * * * *